__US005676153A__

United States Patent [19]
Smith et al.

[11] Patent Number: 5,676,153
[45] Date of Patent: Oct. 14, 1997

[54] SYSTEM AND METHOD FOR DETERMINING SPATIAL ORGANIZATION OF ATRIAL ACTIVATION

[76] Inventors: Joseph M. Smith, 6343 Waterman Ave., St. Louis, Mo. 63130; Gregory W. Botteron, 354 Spring Ave., Webster Grove, Mo. 63119

[21] Appl. No.: 738,329

[22] Filed: Oct. 25, 1996

Related U.S. Application Data

[62] Division of Ser. No. 602,957, Feb. 16, 1996, Pat. No. 5,605,159.

[51] Int. Cl.$^6$ ................................................. A61B 5/0452
[52] U.S. Cl. ........................................................ 128/702
[58] Field of Search ................................. 128/697, 702, 128/705; 607/5

[56] References Cited

U.S. PATENT DOCUMENTS

| | | | |
|---|---|---|---|
| 5,292,348 | 3/1994 | Saumarez et al. | 607/5 |
| 5,366,486 | 11/1994 | Zipes et al. | 128/705 |
| 5,546,951 | 8/1996 | Ben-Haim | 128/702 |

OTHER PUBLICATIONS

*Length of excitation wave and susceptibility to reentrant atrial arrhythmias in normal conscious dogs*, P.L. Rensma, M.A. Allessie, W.J.E.P. Lammers, F.I.M. Bonke, and M.J. Schalij, Circ. Res., vol. 62, pp. 395–410, 1988.

*Pathophysiology of atrial fibrillation*, M.A. Allessie, P.L. Resma, J. Brugada, J.L.R.M. Smeets, O.Penn and C.J.H.J. Kirchoff, Cardiac Electrophysiology from Cell to Bedside, D.P. Zipes and J. Jalife, Eds. Philadelphia: W.B. Saunders, 1990, pp.548–559.

*Circus movement in rabbit atrial muscle as a mechanism of tachycardia. III. The leading circle concept: A new model of cirucs movement in cardiac tissue without the involvement of an anatomic obstacle*, M.A. Allessie, F.I.M. Bonke and F.J.G. Shopman, Circ. Res., vol. 41, pp. 9–18, 1977.

Primary Examiner—William E. Kamm
Assistant Examiner—George R. Evanisko
Attorney, Agent, or Firm—Richard O. Gray, Jr.

[57] ABSTRACT

A system and method evaluates the spatial organization of atrial activation sequences of a heart. Electrical activity of an atrium is sensed at a predetermined number of different localized locations within the atrium to generate a like predetermined number of electrograms. The electrogram generated for each localized location is cross-correlated with the electrograms generated for every other localized location to derive a set of correlation values. A space constant derivable from the correlation values or the correlation values themselves may be used to evaluate antiarrhythmic drug effectiveness or, within an implantable atrial defibrillator, atrial arrhythmia type.

4 Claims, 4 Drawing Sheets

SYSTEM AND METHOD FOR DETERMINING SPATIAL ORGANIZATION OF ATRIAL ACTIVATION

This application is a divisional of U.S. application Ser. No. 08/602,957, now U.S. Pat. No. 5,605,159 filed Feb. 16, 1996, entitled SYSTEM AND METHOD FOR DETERMINING SPATIAL ORGANIZATION OF ATRIAL ACTIVITY.

BACKGROUND OF THE INVENTION

The present invention generally relates to a system and method for determining the extent of spatial organization of atrial activity of the heart. In accordance with additional aspects, the present invention may be utilized to advantage in establishing atrial antiarrhythmic regimens including both appropriate drug screening and selection and chronic electrical cardioverison strategies.

Atrial fibrillation is a common clinical problem, affecting more than one million people in the United States alone, including up to ten percent of those persons over the age of seventy-five. It is the leading cause of cardiogenic embolism and, in the setting of hypertension and/or organic heart disease, is associated with a four to six percent yearly incidents of stroke.

Based upon insights of human studies and animal models, atrial fibrillation is believed to result from rapid and spatially disorganized electrical activity of the atria, with multiple activation wavelets sweeping across the surface of the atria, resulting in an ever-changing pattern of electrical excitation. The absence of coordinated atrial activation and regular, coordinated mechanical contraction, is responsible for the clinical manifestations of atrial fibrillation including loss of hemodynamic efficiency, propensity for thromboembolism, and a rapid, irregular pulse rate.

The preferred clinical end-point for treatment of patients with atrial fibrillation is the restoration and maintenance of normal sinus rhythm with its associated physiologic control of heart rate, preservation of AV synchrony, and reduction of stroke risk. However, this strategy is often frustrated by the inability to prospectively and objectively identify effective antiarrhythmic regimens to prevent recurrences. Additionally, in recent years, the use of antiarrhythmic drugs for atrial fibrillation has been further complicated and attenuated by concerns of potentially life-threatening proarrhythmia associated with empiric drug therapy.

Theoretical consideration, together with results from animal models of atrial fibrillation have suggested that the susceptibility of the atrial electrophysiologic substrate to atrial fibrillation may lend itself to objective, quantitative description. In particular, it has been shown in the dog model that atrial tissue wavelength, $\lambda$, (equal to the product of conduction velocity and tissue refractory) plays a critical role in establishing the susceptibility of the atria to atrial fibrillation, with short $\lambda$ predisposing the atrial fibrillation and long $\lambda$ making atrial fibrillation nonsustainable.

While measurement of $\lambda$ and drug-induced alterations in $\lambda$ may provide an objective strategy for the initial selection of antiarrhythmic agents and subsequent measurement of drug effectiveness, its application in the clinical setting is unfortunately impractical. Its practicality is limited due to the inherent technical difficulties associated with the simultaneous measurement of refractoriness and conduction velocity in the intact human heart.

The present invention provides an objective measurement of the spatial organization of atrial fibrillation to provide an objective assessment of the electrophysiologic substrate and its susceptibility to arrhythmia. This is based upon the proposition that the extent of spatial organization of activation during atrial fibrillation is critically dependent upon the atrial tissue wavelength, $\lambda$. In accordance with the present invention, the measurement of the spatial organization of atrial fibrillation may be conveniently performed within the clinical setting thus making the procedure advantageous for the provision of an objective strategy for the initial selection of anti-arrhythmia agents and subsequent measurement of drug action in vivo. In addition, the determination of the spatial organization of atrial activity, in accordance the present invention, may further be used to advantage in deriving strategies for the electrical cardioversion of atrial arrhythmias with an implantable atrial defibrillator.

SUMMARY OF THE INVENTION

The invention therefore provides a method of evaluating the spatial organization of atrial activation sequences of a heart. The method includes the steps of sensing electrical activity of an atrium of a heart at a predetermined number of different localized locations within the atrium, wherein the localized locations are spaced apart by preselected distances with respect to each other, generating a like predetermined number of electrograms, each electrogram representing the electrical activity sensed at each of the predetermined number of localized locations, and cross-correlating the electrogram generated for each localized location with the electrogram generated for every other localized location to derive a correlation value for each preselected distance.

The method may further include the steps of deriving an average correlation value for each preselected distance and thereafter, deriving a space constant from the average correlation values.

The invention further provides a method of evaluating the effectiveness of a medication upon an atrial arrhythmia of a heart of a patient. The method includes the steps of sensing electrical activity of an atrium of a heart at a predetermined number of different localized location within the atrium, wherein the localized locations are spaced apart by preselected distances with respect to each other, generating a like predetermined number of electrograms, each electrogram representing the electrical activity sensed at each of the predetermined number of localized locations, and cross-correlating the electrogram generated for at least one of the localized locations with the electrogram generated for at least one other one of the localized locations to derive a pre-medication correlation value for at least one of the preselected distances. The method further includes the steps of administering the medication to the patient, after a predetermined period of time repeating the first and second above recited method steps, thereafter cross-correlating the electrogram generated for the at least one of the localized locations with the electrogram generated for the at least other of the localized location to derive a post-medication correlation value for the at least one of the preselected distances, and comparing the pre-medication correlation value to the post-medication correlation value.

The present invention still further provides a method of discriminating between normal sinus rhythm and atrial arrhythmias of a heart. The method includes the steps of sensing electrical activity of an atrium of the heart at at least first and second different localized locations within the atrium, wherein the first and second localized locations are spaced apart by a preselected distance, generating first and second electrograms representing the electrical activity sensed that the first and second localized locations respectively, cross-correlating the first and second electrograms to derive a correlation value, and comparing the correlation value to a predetermined standard.

The present invention still further provides a system for discriminating between normal sinus rhythm and an atrial arrhythmia of atria of a heart. The system includes sensing means for sensing electrical activity of an atrium of the heart at at least first and second different localized locations within the atrium, the first and second localized locations being spaced apart by a preselected distance, means for generating first and second electrograms representing the electrical activity sensed by the sensing means at the first and second localized locations respectively, means for cross-correlating the first and second electrograms to derive a correlation value, and means for comparing the correlation value to a predetermined standard.

The present invention still further provides an atrial cardiovertor/defibrillator comprising criteria establishing means for providing a respective different criteria for each of different types of atrial arrhythmia, therapy means for providing a corresponding therapy to the heart for each of the different types of atrial arrhythmia, and classifying means for identifying one of the types of atrial arrhythmia and causing the therapy means to provide the therapy to the heart corresponding to the identified one of the types of atrial arrhythmia. The classifying means includes sensing means for sensing electrical activity of an atrium of the heart at at least first and second different localized locations within the atrium, the first and second localized locations being spaced apart by a preselected distance, means for generating first and second electrograms representing the electrical activity sensed by the sensing means at the first and second localized locations respectively, means for cross-correlating the first and second electrograms to derive a correlation value, and means for comparing the correlation value to the different criteria.

BRIEF DESCRIPTION OF THE DRAWINGS

The features of the present invention which are believed to be novel are set forth with particularity in the appended claims. The invention, together with further objects and advantage thereof, may be best understood by making reference to the following description taken in conjunction with the accompanying drawing, in several figures of which like referenced numerals identify identical elements, and wherein:

DETAILED DESCRIPTION OF THE PREFERRED EMBODIMENTS

Figure 1:
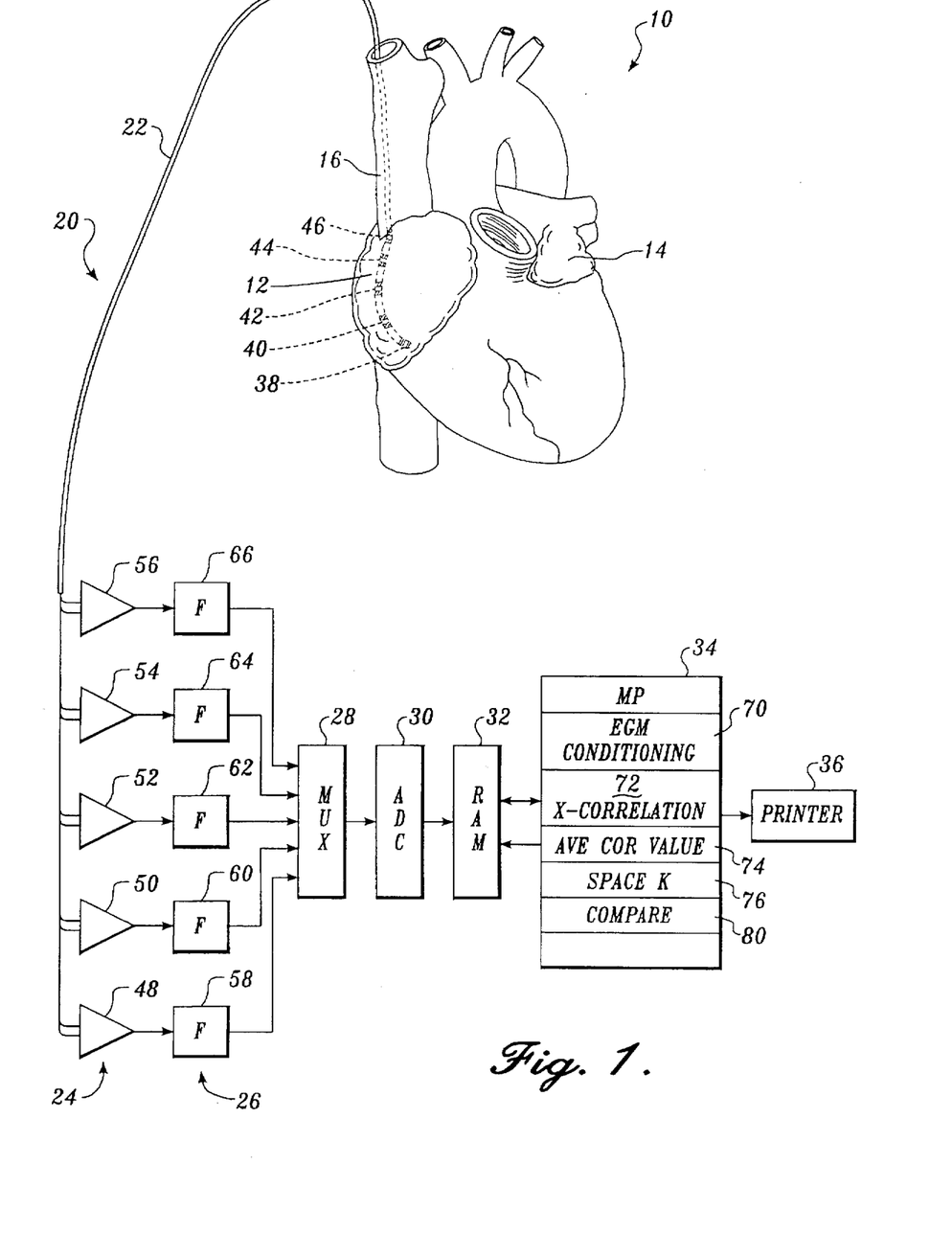
FIG. 1 is a schematic block diagram of a system for evaluating the spatial organization of atrial activity of the atria of a heart in accordance with the present invention.

Referring now to FIG. 1, it illustrates a human heart 10 and a system 20 for evaluating the spatial organization of atrial activation sequences of the atria 12 and 14 of the heart 10 in accordance with the present invention. The system 20 generally includes a temporary catheter 22, a plurality of sense amplifiers 24, a like plurality of bandpass filters 26, a multiplexor 28, and an analog to digital converter 30. The system further includes a random access memory 32, a microprocessor 34, and a printer 36.

The catheter 22 is preferably a decapolar catheter with five electrode pairs 38, 40, 42, 44, and 46. Each electrode is preferably two (2) millimeter in width and the electrodes of each pair are preferably spaced apart by two (2) millimeter. This enables localized sensing of atrial activity at each of the electrode pairs 38, 40, 42, 44, and 46. The electrode pairs preferably are spaced on eleven (11) millimeter centers. The catheter 22 is fed as illustrated down the superior vena cava 16 and into the right atrium 12 for sensing atrial activity of the heart 10 at five different localized locations within the right atrium 12. The localized locations are spaced apart within the atrium 12 by combinations of eleven (11) millimeter, twenty-two (22) millimeter, thirty-three (33) millimeter, and forty-four (44) millimeter.

The plurality of sense amplifiers 26 include five sense amplifiers 48, 50, 52, 54, and 56 having input pairs coupled to the electrode pairs 38, 40, 42, 44, and 46 respectively. Each of the sense amplifiers 48, 50, 52, 54, and 56 generates an electrogram at its output representing the electrical activity sensed by its corresponding respective electrode pair 38, 40, 42, 44, and The plurality of band-pass filters includes band-pass filters 58, 60, 62, 64, and 66. Each band-pass filter preferably has a band-pass of 0.5–400 Hz and has an input coupled to the output of a respective given one of the sense amplifiers 48, 50, 52, 54, and 56. As a result, a band-pass filtered electrogram representing the atrial activity sensed at each of the electrode pairs 38, 40, 42, 44, and 46 is developed at each respective output of the band-pass filters 58, 60, 62, 64, and 66.

The band-pass filtered electrograms are then repeatedly and sequentially applied to the analog to digital converter 30 by the multiplexor 28. The analog to digital converter 30 digitizes the electrograms which are then directly stored in the random access memory 32 for off-line processing by microprocessor 34 as will be described hereinafter. Preferably, the electrograms are sensed, digitized, and stored in the random access memory 32 during a continuous sixty (60) second period to provide a sufficient number of atrial activations upon which to base the spatial organization analysis. The electrogram data stored in the random access memory 32 will be representative of the electrograms sensed by each electrode pair over the sixty (60) second time period.

The microprocessor 34 performs off-line processing and generates analytical results. To that end, the microprocessor executes instructions stored in the random access memory 32 or other memory (not shown) for operating on the electrogram data stored in the random access memory 32. To that end, the instructions define a plurality of operational stages including an electrogram conditioning stage 70, a cross-correlation stage 72, an averaging stage 74, a space constant stage 76, and a compare stage 80.

The electrogram data is first operated upon by the electrogram conditioning stage 70. The electrogram conditioning stage 70 performs digital processing on the electrograms so as to generate a like predetermined number of electrograms with each electrogram representing the sequence of activations sensed at each of the predetermined number of localized locations.

To that end, the operating instructions defining this stage preferably cause the microprocessor to first parse the electrograms into non-overlapping segments of two (2) to ten (10) seconds to maintain, regardless of atrial rhythm, ten (10) to twelve (12) activations in each analysis segment. The data segments are then band-passed filtered using a digital, zero-phase, third order Butterworth filter algorithm with cutoffs of 40–250 Hz. The absolute value of the resulting output of each electrogram is then low-pass filtered using a similar third order Butterworth filter algorithm with a 20 Hz cut-off. This process extracts a time-varying waveform proportional to the amplitude of the high-frequency components (40–250 Hz) in each of the original five electrograms. Each resultant waveform is then normalized to contain unit energy.

The cross-correlation stage 72 then calculates the cross-correlation function between all possible paired combinations of the five electrograms. This results in ten total correlations at four fixed distances being calculated. The cross-correlation of the electrograms is preferably carried out with a standard cross-correlation function. For each data segment, the absolute peak of the cross-correlation function is preferably taken to represent the extent to which activation sequences were correlated for that period of time. The foregoing operation is repeated by the cross-correlation stage 72 on sequential data segments for the entire sixty (60) seconds of stored data for each of the five electrograms. This allows construction of a correlation versus time relationship from which the average correlation over the entire data record can be determined.

The foregoing cross-correlation process derives ten different correlation values, four values for eleven (11) millimeter electrode pair separation, three correlation values for twenty-two (22) millimeter electrode pair separation, two correlation values for thirty-three (33) millimeter electrode pair separation, and only one correlation value for a forty-four (44) millimeter electrode pair separation.

After the correlation values are determined, the values for each given separate distance are averaged by the average correlation value stage 74 to provide a single correlation value for each electrode pair spacing which may be printed out on the printer 36.

Figure 2:
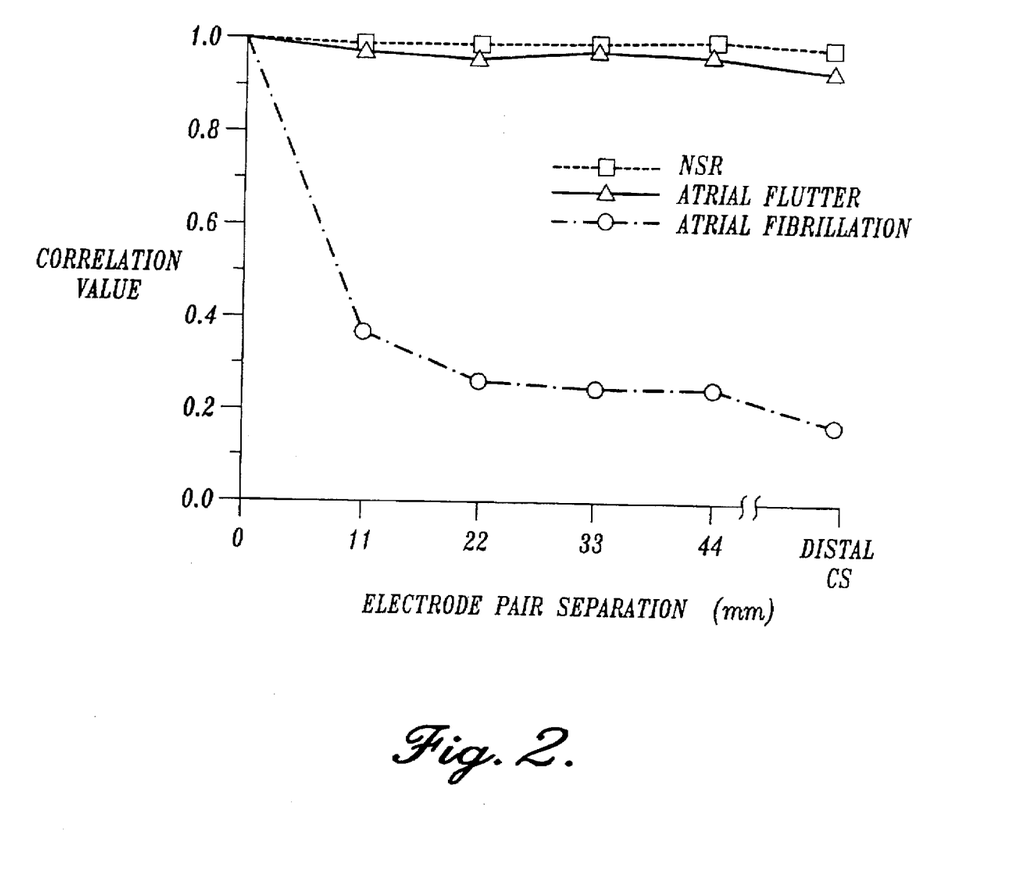
FIG. 2 is a graph plotting correlation values derived in accordance with the present invention versus sensing location spacing for normal sinus rhythm, atrial flutter, and atrial fibrillation.

FIG. 2 is a graph, plotting correlation value versus distance obtained as described above for the same patient during normal sinus rhythm, atrial flutter, and atrial fibrillation. It can be noted that during normal sinus rhythm, the correlation value for all electrode pair spacing is essentially unity and only slightly less during atrial flutter. This indicates that during normal sinus rhythm and atrial flutter, there is a high degree of spatial organization. However, during atrial fibrillation, it will be noted that the correlation value is substantially less than unity for all electrode pair spacing. Hence, during atrial fibrillation, there is a comparatively low degree of spatial organization. These differences in correlation values, as will be seen hereinafter, may be utilized to advantage in discriminating between normal sinus rhythm and atrial arrhythmias.

Additional information may be further derived from the graph of FIG. 2, namely the space constant ($\delta$) which is a proportional measure of the previously referred to atrial tissue wavelength ($\lambda$). The reason the space constant may be considered an estimate of the atrial tissue wavelength is because the relation between the spatial organization of activation during atrial fibrillation and the atrial tissue wavelength is a natural consequence of the wavelet hypothesis of atrial fibrillation. At any point in time for each wavelet on the surface of the atria, there is a region of tissue under the direct influence of that wavelet (i.e., that wavelet's domain). Within the wavelet's domain, activations are well correlated, having been initiated by this one wavelet. The area of that domain varies over time and space, but at any instant, within the domain there must be a self-avoiding path (the wake of the wavelet) with a link equal to or greater than the atrial tissue wavelength. In the limit of leading circle reentry, the minimum area for the domain of a wavelet would then be the area of the circle with circumference equal to the atrial tissue wavelength. Hence, atrial activation sequences within a small region are well correlated while activation sequences beyond some distance are no longer well correlated (reflective of their participation in different wavelets). The space constant (the distance over which activation sequences are well correlated) can then serve as an objective measure for a spatial organization of electrical activation during atrial fibrillation as well as an estimator of atrial tissue wavelength.

To derive the space constant during atrial fibrillation, the correlation values versus distance graph of FIG. 2 for atrial fibrillation may be approximated by the space constant stage 76 as a decaying exponential function of, $CC(d)=-d/\delta$ where $CC(d)$ is the cross-correlation value as a function of distance, d is the electrode pair spacing, and $\delta$ is the space constant. The space constant, $\delta$, may be determined by the space constant stage 16 by determining the statistical best fit $\delta$ for each data set by finding the value of $\delta$ which minimizes the waited mean-squared error between the exponential function and the data where the waiting function for each value of cross-correlation is equal to the number of observations available at that point. Thus, the measure of correlation for eleven (11) millimeter electrode pair spacing is the average of four measures, with error at the point waited by four, while that for forty-four (44) millimeter electrode pair spacing is a single measure, with the error at that point receiving unity waiting.

The value of $\delta$ determined in this fashion serves as a single objective and quantitative measure of the extent of spatial organization of activation sequences during atrial arrhythmias in general, and during atrial fibrillation in particular. As will be noted from FIG. 2, during normal sinus rhythm and atrial flutter, the space constant is infinitely large with respect to the size of the atria. However, during atrial fibrillation, the space constant is monotonically decreasing with increasing electrode pair spacing. The difference in the space constant may be utilized to advantage in discriminating between normal sinus rhythm and atrial arrhythmias.

Figure 3:
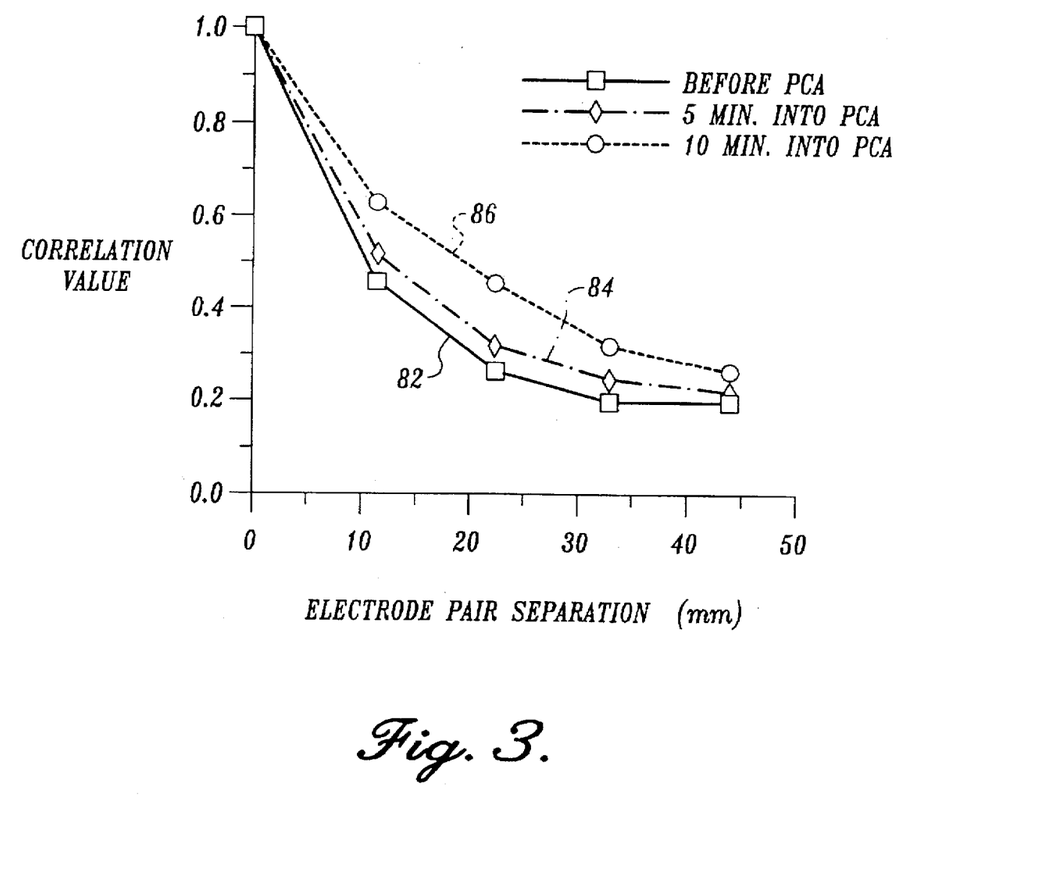
FIG. 3 is a graph plotting correlation values derived in accordance with the present invention versus sensing location spacing for pre-medication atrial activity and post-medication atrial activity to illustrate the manner in which the present invention may be utilized to advantage in the screening of antiarrhythmic drugs.

Referring now to FIG. 3, it is a graph of correlation values versus electrode pair separation to illustrate the utility of the present invention in the screening of antiarrhythmic drugs. A first plot 82 displays the correction values from electrograms obtained during atrial fibrillation and before administration of the antiarrhythmic drug Procainamide (PCA) to the patient. Plots 84 and 86 display the correlation values from electrograms obtained during atrial fibrillation at five (5) and ten (10) minute intervals respectively after PCA was administered. All correlation values illustrated in FIG. 3 were derived in the manner as previously described in connection with the discussion of FIG. 1.

As will be noted in FIG. 3, after PCA was administered, there was a prominent increase in the correlation values for all electrode pair separations. Since the correlation values increased with time, the spatial organization of the atria increased and the medication, given these results, was known to be effective for this patient. It also naturally follows that the space constant was increased and may be calculated from the correlation values of plots 82, 84 and 86 in a manner as previously described. Deriving the space constants has the increased reliability of simultaneously taking into account all of the correlation values generated for each plot. However, the results of FIG. 3 demonstrably show that any one electrode separation may be relied upon for the screening process requiring just two electrode pairs at almost any known separation between, for example, ten (10) millimeter and forty-four (44) millimeter. In this way, only two pair of electrograms need be taken, one pair of electrograms prior to administration of the medication for the generation of a pre-medication correlation value and the other pair of electrograms after administration of the medication for the generation of a post-medication correlation value. The post-medication correlation value can then be compared to the pre-medication correlation value by the compare stage 80 of the microprocessor 34 (FIG. 1). The results may then be printed by the printer 36 to indicate the effectiveness of the medication. Preferably, the results include the premedication and post-medication correlation values.

Figure 4:
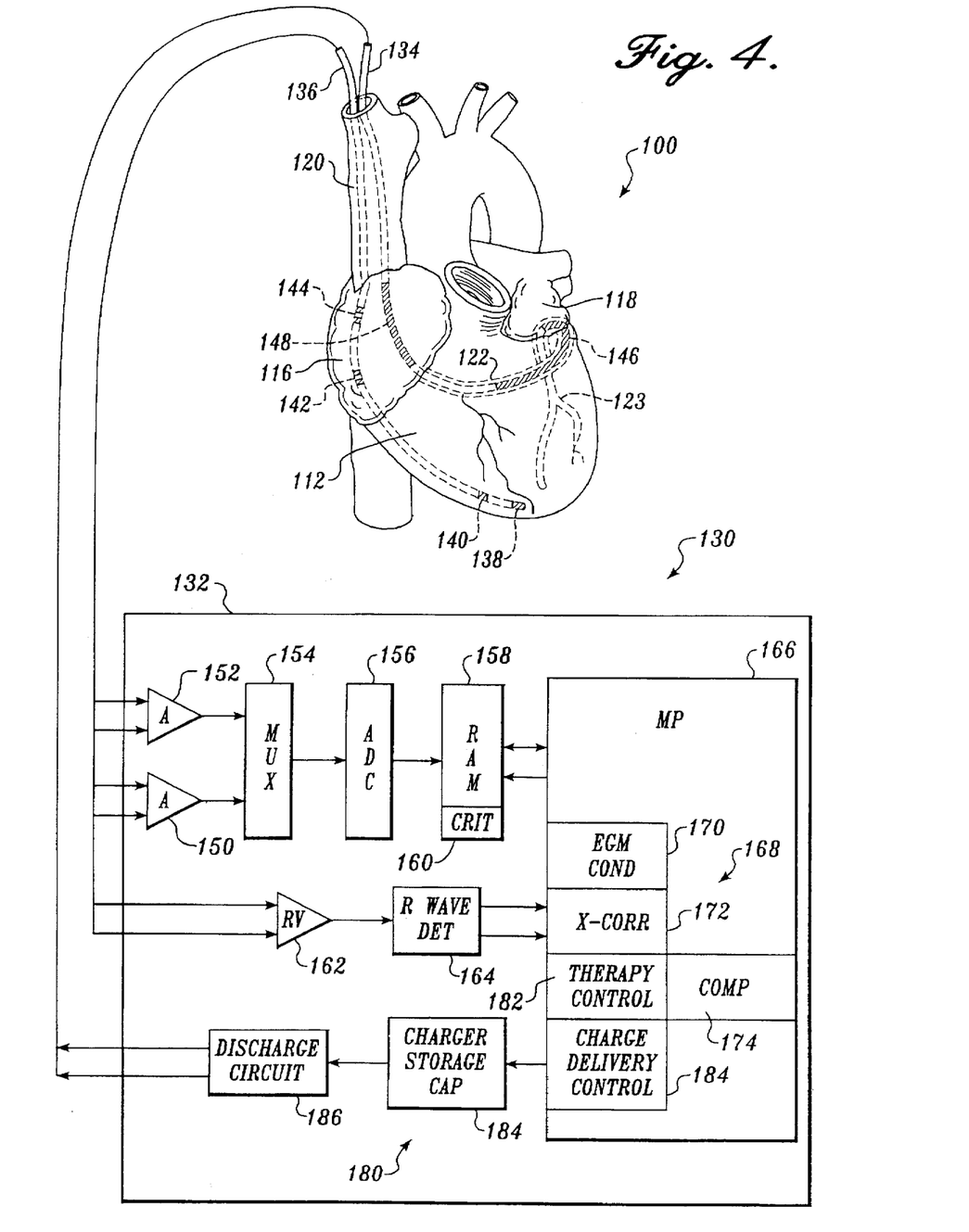
FIG. 4 is a schematic block diagram of an implantable atrial defibrillator embodying the present invention shown in association with a human heart in need of atrial arrhythmia monitoring, atrial arrhythmia classifying, and potential atrial cardioverting.

Referring now to FIG. 4, it illustrates an implantable automatic atrial defibrillator 130 embodying the present invention. It is shown associated with a heart 100 in need of atrial arrhythmia monitoring and potential cardioversion.

The atrial defibrillator 130 includes an implantable enclosure 132 and an implantable lead system including an intravascular lead 134 and an endocardial lead 136. The endocardial lead 136 has tip and ring electrodes 138 and 140 respectively adapted for placement in the right ventricle 112. The endocardial lead 136 further includes proximal electrode pairs 142 and 144, each pair of electrodes for sensing localized activity to the right atria 116. The electrode pairs 142 and 144 are preferably structured as previously described and separated by an interelectrode spacing of twenty-two (22) millimeter, for example.

The intravasuclar lead 134 has a tip electrode 146 adapted for placement in the coronary sinus 122 or the great cardiac vein 123 and a ring electrode 148 adapted for placement in the superior vena cava 120 or right atrium 116. An alternate lead system may include separate leads for electrodes 146 and 148.

Electrode pairs 142 and 144 of lead 136 sense localized atrial activity of the heart. Electrodes 146 and 148 of lead 134 perform the function of applying cardioverting electrical energy across the right and left artia 116 and 118 of the heart. Electrodes 138 and 140 sense localized activity of the right ventricle 112 to enable detection of R waves for synchronizing the application of the cardioverting energy to the atria with an R wave.

Within the enclosure 132, the atrial defibrillator 130 includes sense amplifiers 150 and 152, multiplexor 154, analog to digital converter 156, and random access memory 158. Sense amplifier 150 is couple to the electrode pair 142 and sense amplifier 152 is couple to the electrode pair 144. The sense amplifiers 150 and 152 generate electrogram signals representing the localized activity sensed by electrode pairs 142 and 144 respectively to provide electrograms for cross-correlation after electrogram conditioning. The cross-correlation of the electrograms may be performed as previously described to derive a correlation value. The correlation value can when be compared to atrial arrhythmia criteria stored in a memory portion 160 of random access memory 158 to determine if the atria are in normal sinus rhythm, atrial flutter, or atrial fibrillation.

Another sense amplifier 162 is coupled to electrodes 138 and 140 of lead 136. The sense amplifier 162 has an output coupled to an R wave detector 164 of the type well known in the art for isolating R waves. The R wave detection of the detector 164 enables the cardioverting electrical energy to be applied to the atria in synchronism with an R wave of the right ventricle.

The outputs of the sense amplifiers 150 and 152 are coupled to the analog to digital converter 156 through the multiplexor 154. The analog to digital converter 156 digitizes the electrograms provided by the amplifiers 150 and 152 to generate electrogram digital data samples. Electrogram 'samples are then conveyed to the random access memory 150. The sense amplifiers 150 and 152 each preferably includes a filter for prefiltering the atrial electrograms prior to multiplexing as previously described in connection with FIG. 1.

A microprocessor 166 implements an atrial arrhythmia detector and discriminator 168 responsive to the atrial electrogram digital sample stored in the random access memory 158. To that end, the microprocessor 166 implements the electrogram conditioning 170 and the cross-correlation 172 in a manner as previously described. Hence, atrial activity is sensed for a period of, for example, sixty (60) seconds, and the electrograms representing the atrial activity for the sixty (60) second period are conditioned by the electrogram conditioning stage 170 and then cross-correlated by the cross-correlation stage 172 as previously described to derive a correlation value.

The atrial arrhythmia criteria stored in memory portion 160 of random access memory 158 may be representative of predetermined correlation values representing correlation value ranges representing normal sinus rhythm, atrial flutter, and atrial fibrillation. When the cross-correlation stage 172 derives the correlation value, the microprocessor through a compare stage 174 compares the correlation value to the correlation value ranges stored in memory portion 160. In this manner, the microprocessor 166 determines whether the heart is in normal sinus rhythm, atrial flutter, or atrial fibrillation.

The cardioverting stage 180 provides a different cardioverting therapy for each respective different type of atrial arrhythmia. The cardioverting stage 180 includes a therapy control 182 and a charge and delivery control 184 implemented by the microprocessor 166 and a charger and storage capacitor circuit 184 and discharge circuit 186. The therapy control 182 responsive to the atrial arrhythmia type detected by the comparator 174 selects a corresponding one of the available atrial therapies. For example, for atrial fibrillation, the therapy may include a relatively high voltage cardioverting discharge to the atria while for atrial flutter, the therapy may include a relatively low voltage cardioverting discharge to the atria. Upon determining which therapy to deliver, the therapy control 182 controls the charge delivery control 184 so that the storage capacitor of circuit 184 is charged to a voltage appropriate for the atrial arrhythmia type. When the capacitor of circuit 184 is charged to the appropriate voltage, the discharge circuit 186 discharges the voltage stored in the capacitor of circuit 184 in synchronise with an R wave detected by the R wave detector 164. The discharged voltage is applied across electrodes 146 and 148 of lead 134 for cardioverting the atria.

While particular embodiments of the present invention have been shown and described, modifications may be made. For example, the system and method of the present invention may be used to advantage in implantable automatic atrial defibrillators of the type which provide a respective and corresponding therapy for each of different types of atrial fibrillation. Such an implantable atrial defibrillator is disclosed, for example, in co-pending application Ser. No. 08/331,898 filed Oct. 31, 1994 for ATRIAL FIBRILLATION TYPE SELECTIVE CARDIOVERTER AND METHOD. Hence, it is therefore intended to cover in the appended claims all such changes and modifications which fall within the true spirit and scope of the invention.

What is claimed is:

1. A method for use in evaluating the spatial organization of atrial activation sequences of a heart, said method including the steps of:

sensing electrical activity of an atrium of a heart at a predetermined number of different localized locations within the atrium, the localized locations being spaced apart by preselected distances with respect to each other;

generating a like predetermined number of electrograms, each electrogram representing the electrical activity sensed at each of the predetermined number of localized locations; and cross-correlating the electrogram generated for each localized location with the electrogram generated for every other localized location to derive a correlation value for each preselected distance.

2. A method as defined in claim 1 including the further steps of deriving an average correlation value for each preselected distance and thereafter, deriving a space constant from the average correlation values.

3. A method for use in discriminating between normal sinus rhythm and at least one atrial arrhythmia of a heart, said method including the steps of:

sensing electrical activity of an atrium of the heart at at least first and second different localized locations within the atrium, the first and second localized locations being spaced apart by a preselected distance;

generating first and second electrograms representing the electrical activity sensed at the first and second localized locations respectively;

cross-correlating the first electrogram to the and second electrogram to derive a correlation value; and comparing the correlation value to a predetermined standard.

4. A system for use in discriminating between normal sinus rhythm and an atrial arrhythmia of atria of a heart, said system comprising:

sensing means for sensing electrical activity of an atrium of the heart at at least first and second different localized locations within the atrium, the first and second localized locations being spaced apart by a preselected distance;

means for generating first and second electrograms representing the electrical activity sensed by said sensing means at the first and second localized locations respectively;

means for cross-correlating the first electrogram to the and second electrogram to derive a correlation value; and means for comparing the correlation value to a predetermined standard.

* * * * *

UNITED STATES PATENT AND TRADEMARK OFFICE
CERTIFICATE OF CORRECTION

PATENT NO. : 5,676,153
DATED : October 14, 1997
INVENTOR(S) : Joseph M. Smith and Gregory W. Botteron It is certified that error appears in the above-identified patent and that said Letters Patent is hereby corrected as shown below:

| Column | Line | |
|--------|------|---|
| 4 | 28 | insert --46-- after "and" |
| 7 | 46 | "artia" should be --atria-- |
| 7 | 62 | "when" should be --then-- |
| 8 | 11 | delete --'--before "samples" |

Signed and Sealed this

Tenth Day of March, 1998

Attest:

BRUCE LEHMAN

*Attesting Officer*      *Commissioner of Patents and Trademarks*